(12) United States Patent  (10) Patent No.: US 7,927,372 B2
Griffis, III et al.  (45) Date of Patent: Apr. 19, 2011

(54) SCLERAL PROSTHESIS HAVING CROSSBARS FOR TREATING PRESBYOPIA AND OTHER EYE DISORDERS

(75) Inventors: Jack C. Griffis, III, Decatur, GA (US); Mark A. Cox, Dallas, TX (US); Douglas C. Williamson, Coppell, TX (US); Peter J. Richardson, Buckinghamshire (GB); Barrie D. Soloway, Long Beach, NY (US)

(73) Assignee: Refocus Group, Inc., Dallas, TX (US)

( * ) Notice: Subject to any disclaimer, the term of this patent is extended or adjusted under 35 U.S.C. 154(b) by 20 days.

(21) Appl. No.: 12/183,237

(22) Filed: Jul. 31, 2008

(65) Prior Publication Data

US 2009/0099654 A1 Apr. 16, 2009

Related U.S. Application Data

(60) Provisional application No. 60/963,073, filed on Aug. 2, 2007.

(51) Int. Cl.
 A61F 2/14 (2006.01)
 A61F 9/013 (2006.01)
 A61F 9/00 (2006.01)
(52) U.S. Cl. .......................................................... 623/4.1
(58) Field of Classification Search .................. 623/4.1, 623/6.64, 17.5, 21.18, 17.15; 604/8; 368/293
 See application file for complete search history.

(56) References Cited

U.S. PATENT DOCUMENTS

| | | | |
|---|---|---|---|
| 2,645,878 A * | 7/1953 | Johnson | 446/137 |
| 2,952,023 A | 9/1960 | Rosen | |
| 3,064,643 A | 11/1962 | Dixon | |
| 3,454,966 A | 7/1969 | Rosen | |
| D227,386 S * | 6/1973 | Wood | D21/560 |
| 3,884,236 A | 5/1975 | Krasnov | |
| 3,965,613 A * | 6/1976 | Saunders | 446/132 |
| 3,996,935 A | 12/1976 | Banko | |
| 4,174,389 A | 11/1979 | Cope | |
| 4,391,275 A | 7/1983 | Fankhauser et al. | |

(Continued)

FOREIGN PATENT DOCUMENTS

DE 4232021 4/1994

(Continued)

OTHER PUBLICATIONS

Ronald A. Schachar, MD, PhD, "Cause and Treatment of Presbyopia with a Method for Increasing the Amplitude of Accommodation", Annals of Ophthalmology, Dec. 1992, pp. 445-447, 452.

(Continued)

Primary Examiner — David H Willse
Assistant Examiner — Tiffany Shipmon (57) ABSTRACT

A scleral prosthesis includes a prosthesis body having first and second side surfaces and a cavity extending through the prosthesis body from the first side surface to the second side surface. The scleral prosthesis also includes a crossbar configured to be inserted into the cavity, where the crossbar is wider than the prosthesis body. The cavity could define a narrower central opening and wider end openings, and the crossbar could have a narrower central portion and wider end portions. Also, the prosthesis body could include multiple cavities, and the scleral prosthesis could include multiple crossbars configured to be inserted into the multiple cavities. Each of the cavities could be located proximate to an end of the prosthesis body. The crossbar could be substantially straight with a cylindrical cross section.

21 Claims, 6 Drawing Sheets

U.S. PATENT DOCUMENTS

| | | | |
|---|---|---|---|
| 4,452,235 A | 6/1984 | Reynolds | |
| 4,521,210 A | 6/1985 | Wong | |
| 4,549,529 A | 10/1985 | White | |
| 4,603,697 A | 8/1986 | Kamerling | |
| 4,782,820 A | 11/1988 | Woods | |
| 4,839,342 A | 6/1989 | Kaswan | |
| 4,846,172 A | 7/1989 | Berlin | |
| 4,907,586 A | 3/1990 | Bille et al. | |
| 4,923,699 A | 5/1990 | Kaufman | |
| 4,946,436 A | 8/1990 | Smith | |
| 4,961,744 A | 10/1990 | Kilmer et al. | |
| 4,966,452 A | 10/1990 | Shields et al. | |
| 4,993,985 A * | 2/1991 | Bass et al. | 446/133 |
| 5,022,413 A | 6/1991 | Spina, Jr. et al. | |
| 5,025,811 A | 6/1991 | Dobrogowski et al. | |
| 5,098,443 A | 3/1992 | Parel et al. | |
| 5,109,846 A | 5/1992 | Thomas | |
| 5,152,759 A | 10/1992 | Parel et al. | |
| 5,152,760 A | 10/1992 | Latina | |
| 5,163,419 A | 11/1992 | Goldman | |
| 5,174,304 A | 12/1992 | Latina et al. | |
| 5,181,922 A | 1/1993 | Blumenkanz et al. | |
| 5,246,435 A | 9/1993 | Bille et al. | |
| 5,267,553 A | 12/1993 | Graether | |
| 5,292,514 A | 3/1994 | Capecchi et al. | |
| 5,300,114 A | 4/1994 | Gwon et al. | |
| 5,300,144 A | 4/1994 | Adams | |
| 5,312,394 A | 5/1994 | Beckman | |
| 5,323,788 A | 6/1994 | Silvestrini et al. | |
| 5,354,331 A | 10/1994 | Schachar | |
| 5,372,595 A | 12/1994 | Gaasterland et al. | |
| 5,439,462 A | 8/1995 | Bille et al. | |
| 5,443,505 A | 8/1995 | Wong et al. | |
| 5,472,436 A | 12/1995 | Fremstad | |
| 5,476,511 A | 12/1995 | Gwon et al. | |
| 5,520,631 A | 5/1996 | Nordquist et al. | |
| 5,529,076 A | 6/1996 | Schachar | |
| 5,558,630 A | 9/1996 | Fisher | |
| RE35,390 E | 12/1996 | Smith | |
| 5,766,242 A | 6/1998 | Wong et al. | |
| 5,824,086 A | 10/1998 | Silvestrini | |
| RE35,974 E | 12/1998 | Davenport et al. | |
| 5,879,319 A | 3/1999 | Pynson et al. | |
| 6,007,578 A | 12/1999 | Schachar | |
| 6,197,056 B1 | 3/2001 | Schachar | |
| 6,206,919 B1 | 3/2001 | Lee | |
| 6,217,571 B1 | 4/2001 | Peyman | |
| 6,280,468 B1 | 8/2001 | Schachar | |
| 6,299,640 B1 | 10/2001 | Schachar | |
| 6,527,780 B1 | 3/2003 | Wallace et al. | |
| 6,641,614 B1 * | 11/2003 | Wagner et al. | 623/17.15 |
| 6,712,847 B2 * | 3/2004 | Baikoff et al. | 623/4.1 |
| 6,910,939 B2 * | 6/2005 | Hui | 446/93 |
| 7,008,396 B1 * | 3/2006 | Straub | 604/8 |
| 7,416,560 B1 | 8/2008 | Schachar | |
| 2002/0002403 A1 | 1/2002 | Zdenek | |
| 2002/0010509 A1 | 1/2002 | Schachar | |
| 2002/0026239 A1 | 2/2002 | Schachar | |
| 2002/0035397 A1 * | 3/2002 | Baikoff | 623/4.1 |
| 2004/0054374 A1 | 3/2004 | Weber et al. | |
| 2005/0283233 A1 * | 12/2005 | Schachar | 623/4.1 |
| 2006/0129129 A1 | 6/2006 | Smith | |
| 2008/0091266 A1 | 4/2008 | Griffis, III et al. | |

FOREIGN PATENT DOCUMENTS

| | | |
|---|---|---|
| EP | 0 083 494 | 7/1983 |
| EP | 0 262 893 | 4/1988 |
| FR | 2 784 287 | 4/2000 |
| FR | 2 791 552 | 10/2000 |
| GB | 1456746 | 11/1976 |
| SG | 65893 | 3/2001 |
| SU | 1538914 | 1/1990 |
| SU | 1597188 | 10/1990 |
| SU | 1639647 | 4/1991 |
| TW | 82609 | 11/1986 |
| TW | 128961 | 4/1995 |
| WO | WO 89/09034 | 10/1989 |
| WO | WO 91/14406 A1 | 10/1991 |
| WO | WO 94/02084 | 2/1994 |
| WO | WO 94/03129 | 2/1994 |
| WO | WO 94/06381 | 3/1994 |
| WO | WO 94/06504 | 3/1994 |
| WO | WO 95/03755 | 2/1995 |
| WO | WO 95/28984 A1 | 11/1995 |
| WO | WO 96/40005 | 12/1996 |
| WO | WO 98/42409 | 10/1998 |
| WO | WO 99/17691 A1 | 4/1999 |
| WO | WO 99/30645 | 6/1999 |
| WO | WO 99/30656 | 6/1999 |
| WO | WO 00/21466 A1 | 4/2000 |
| WO | WO 00/40174 | 7/2000 |
| WO | WO 00/59406 | 10/2000 |
| WO | WO 00/74600 | 12/2000 |
| WO | WO 01/17460 | 3/2001 |
| WO | WO 01/45607 | 6/2001 |
| WO | WO 02/067830 A1 | 9/2002 |
| WO | WO 2006/014484 A2 | 2/2006 |
| ZA | 98/4634 | 2/1999 |
| ZA | 98/9149 | 6/1999 |

OTHER PUBLICATIONS

European Search Report dated Jul. 18, 2008 in connection with European Patent Application No. 06 00 7630.

Office Action dated Apr. 15, 2008 in connection with Canadian Patent Application No. 2,274,260.

Spencer P. Thornton, "Anterior Ciliary Sclerotomy (ACS), A Procedure to Reverse Presbyopia", Surgery for Hyperopia and Presbyopia, 1997, pp. 33-36.

Annex to Form PCT/ISA/206 Communication Relating to the Results of the Partial International Search dated Apr. 10, 2008 in PCT Application No. PCT/US2007/015774.

Notification of Transmittal of the International Search Report and the Written Opinion of the International Searching Authority, or the Declaration dated Nov. 7, 2008 in connection with PCT Application No. PCT/US2007/015774.

Notification of Transmittal of the International Search Report and the Written Opinion of the International Searching Authority, or the Declaration dated Oct. 1, 2008 in connection with PCT Application No. PCT/US2008/071750.

Office Action dated Jan. 8, 2009 in connection with U.S. Appl. No. 09/972,533.

* cited by examiner

SCLERAL PROSTHESIS HAVING CROSSBARS FOR TREATING PRESBYOPIA AND OTHER EYE DISORDERS

PRIORITY CLAIM AND CROSS-REFERENCE TO RELATED PATENT DOCUMENTS

This application claims priority under 35 U.S.C. §119(e) to U.S. Provisional Patent Application No. 60/963,073 filed on Aug. 2, 2007, which is hereby incorporated by reference.

This application is related to the following U.S. patent applications and issued patents:

(1) U.S. Pat. No. 6,007,578 entitled "Scleral Prosthesis for Treatment of Presbyopia and Other Eye Disorders" issued on Dec. 28, 1999;
(2) U.S. Pat. No. 6,280,468 entitled "Scleral Prosthesis for Treatment of Presbyopia and Other Eye Disorders" issued on Aug. 28, 2001;
(3) U.S. Pat. No. 6,299,640 entitled "Scleral Prosthesis for Treatment of Presbyopia and Other Eye Disorders" issued on Oct. 9, 2001;
(4) U.S. Pat. No. 5,354,331 entitled "Treatment of Presbyopia and Other Eye Disorders" issued on Oct. 11, 1994;
(5) U.S. Pat. No. 5,465,737 entitled "Treatment of Presbyopia and Other Eye Disorders" issued on Nov. 14, 1995;
(6) U.S. Pat. No. 5,489,299 entitled "Treatment of Presbyopia and Other Eye Disorders" issued on Feb. 6, 1996;
(7) U.S. Pat. No. 5,503,165 entitled "Treatment of Presbyopia and Other Eye Disorders" issued on Apr. 2, 1996;
(8) U.S. Pat. No. 5,529,076 entitled "Treatment of Presbyopia and Other Eye Disorders" issued on Jun. 25, 1996;
(9) U.S. Pat. No. 5,722,952 entitled "Treatment of Presbyopia and Other Eye Disorders" issued on Mar. 3, 1998;
(10) U.S. Pat. No. 6,197,056 entitled "Segmented Scleral Band for Treatment of Presbyopia and Other Eye Disorders" issued on Mar. 6, 2001;
(11) U.S. Pat. No. 6,579,316 entitled "Segmented Scleral Band for Treatment of Presbyopia and Other Eye Disorders" issued on Jun. 17, 2003;
(12) U.S. Pat. No. 6,926,727 entitled "Surgical Blade for Use with a Surgical Tool for Making Incisions for Scleral Eye Implants" issued on Aug. 9, 2005;
(13) U.S. Pat. No. 6,991,650 entitled "Scleral Expansion Device Having Duck Bill" issued on Jan. 31, 2006;
(14) U.S. patent application Ser. No. 10/080,877 entitled "System and Method for Making Incisions for Scleral Eye Implants" filed on Feb. 22, 2002;
(15) U.S. patent application Ser. No. 10/443,122 entitled "System and Method for Determining a Position for a Scleral Pocket for a Scleral Prosthesis" filed on May 20, 2003;
(16) U.S. patent application Ser. No. 11/137,085 entitled "Scleral Prosthesis for Treatment of Presbyopia and Other Eye Disorders" filed on May 24, 2005;
(17) U.S. patent application Ser. No. 11/199,591 entitled "Surgical Blade for Use with a Surgical Tool for Making Incisions for Scleral Eye Implants" filed on Aug. 8, 2005;
(18) U.S. patent application Ser. No. 11/252,369 entitled "Scleral Expansion Device Having Duck Bill" filed on Oct. 17, 2005;
(19) U.S. patent application Ser. No. 11/323,283 entitled "Surgical Blade for Use with a Surgical Tool for Making Incisions for Scleral Eye Implants" filed on Dec. 30, 2005;
(20) U.S. patent application Ser. No. 11/323,284 entitled "System and Method for Making Incisions for Scleral Eye Implants" filed on Dec. 30, 2005;
(21) U.S. patent application Ser. No. 11/322,728 entitled "Segmented Scleral Band for Treatment of Presbyopia and Other Eye Disorders" filed on Dec. 30, 2005;
(22) U.S. patent application Ser. No. 11/323,752 entitled "Segmented Scleral Band for Treatment of Presbyopia and Other Eye Disorders" filed on Dec. 30, 2005;
(23) U.S. Provisional Patent Application No. 60/819,995 entitled "Apparatuses, Systems, and Methods Related to Treating Presbyopia and Other Eye Disorders" filed on Jul. 11, 2006;
(24) U.S. patent application Ser. No. 11/827,444 entitled "Apparatus and Method for Securing Ocular Tissue" filed on Jul. 11, 2007; and
(25) U.S. patent application Ser. No. 11/827,382 entitled "Scleral Prosthesis for Treating Presbyopia and Other Eye Disorders and Related Devices and Methods" filed on Jul. 11, 2007.

All of these U.S. patents and patent applications are hereby incorporated by reference.

TECHNICAL FIELD

This disclosure is generally directed to eye implants and more specifically to a scleral prosthesis having crossbars for treating presbyopia and other eye disorders.

BACKGROUND

It is possible to treat presbyopia, glaucoma, and other eye disorders by implanting scleral prostheses within the sclera of a patient's eye. For each individual scleral prosthesis, an incision is made in the sclera of the patient's eye. The incision is then extended under the surface of the sclera to form a scleral "tunnel," and a scleral prosthesis is placed within the tunnel. One or multiple scleral prostheses may be implanted in a patient's eye to (among other things) treat presbyopia, glaucoma, ocular hypertension, elevated intraocular pressure, macular degeneration, or other eye disorders. This technique is described more fully in the patents documents incorporated by reference above.

SUMMARY

This disclosure provides a scleral prosthesis having crossbars for treating presbyopia and other eye disorders.

In a first embodiment, a scleral prosthesis includes a prosthesis body having first and second side surfaces and a cavity extending through the prosthesis body from the first side surface to the second side surface. The scleral prosthesis also includes a crossbar configured to be inserted into the cavity, the crossbar wider than the prosthesis body.

In a second embodiment, a scleral prosthesis body includes first and second free ends and first and second side surfaces. The scleral prosthesis body also includes a cavity extending through the scleral prosthesis body from the first side surface to the second side surface, where the cavity is configured to receive a crossbar inserted through the cavity.

In a third embodiment, a method includes inserting a scleral prosthesis body into ocular tissue of a patient's eye. The method also includes inserting a crossbar into a cavity of the scleral prosthesis body. The crossbar is wider than the scleral prosthesis body, and the cavity extends through the scleral prosthesis body from a first side surface to a second side surface of the scleral prosthesis body.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawing, in which.

DETAILED DESCRIPTION

FIGS. 1 through 6, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1A:
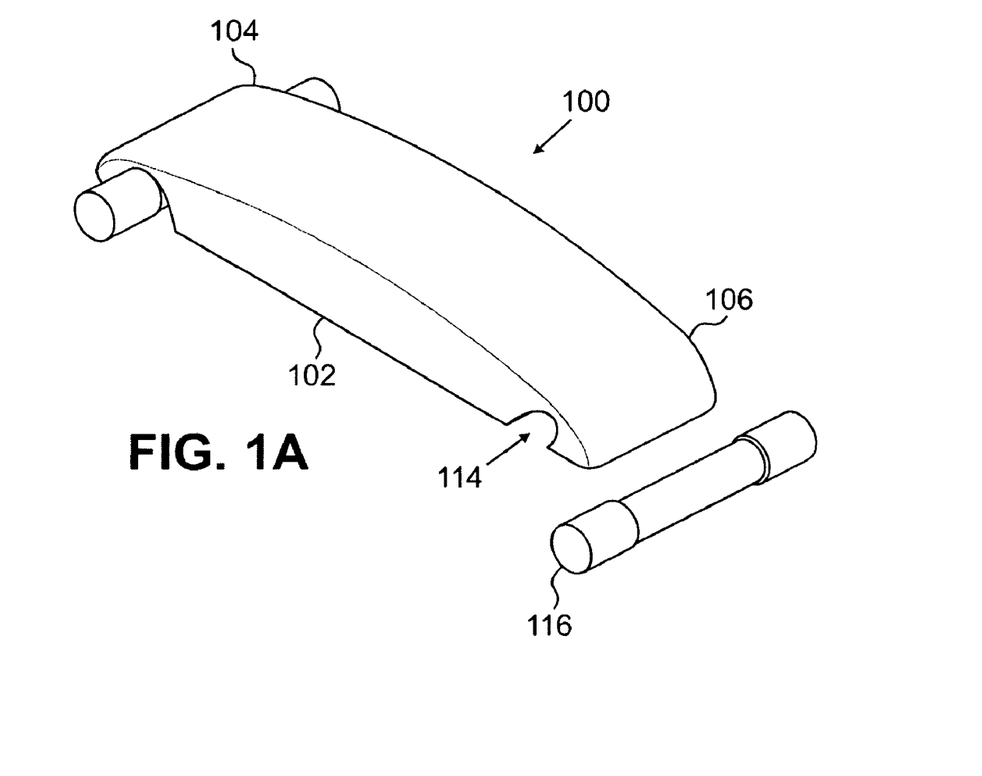
FIGS. 1A and 1B illustrate an example scleral prosthesis having crossbars in accordance with this disclosure.
Figure 1B:
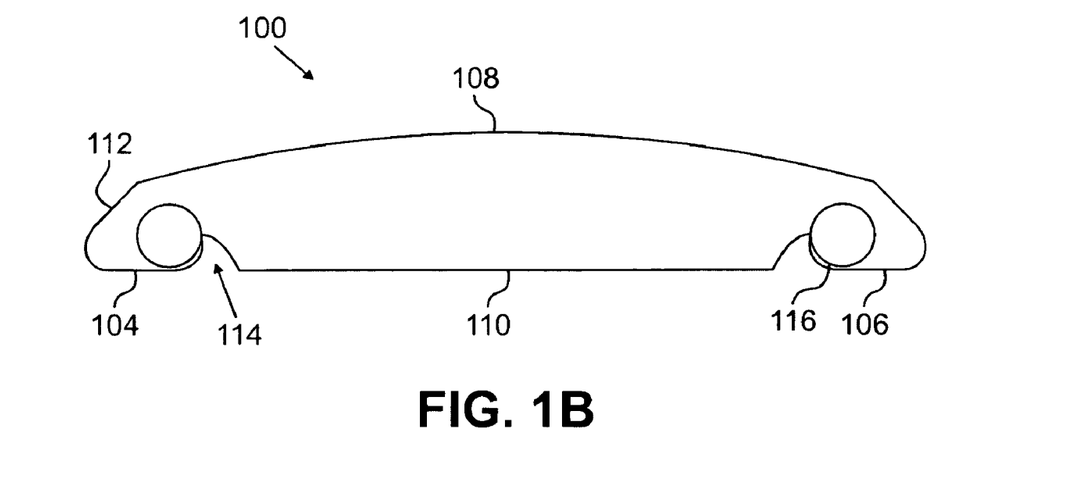

FIGS. 1A and 1B illustrate an example scleral prosthesis 100 having crossbars in accordance with this disclosure. The embodiment of the scleral prosthesis 100 shown in FIGS. 1A and 1B is for illustration only. Other embodiments of the scleral prosthesis 100 could be used without departing from the scope of this disclosure.

As shown in FIGS. 1A and 1B, the scleral prosthesis 100 includes a body 102 having opposing ends 104-106, a top surface 108, and a bottom surface 110. In this example, the top surface 108 is generally convex and reaches a peak at or near the middle of the body 102. Also, the top surface 108 includes concave portions 112 at the ends 104-106 of the body 102. In addition, in this example, the bottom surface 110 is generally flat. However, the top surface 108 and the bottom surface 110 of the body 102 could have any other suitable sizes or shapes, such as when at least a portion of the bottom surface 110 is curved.

As shown here, the body 102 of the scleral prosthesis 100 also includes one or more notches 114 that can receive one or more crossbars 116. The notches 114 represent areas of the body 102 into which the crossbars 116 can be at least partially inserted or retained. For example, the notches 114 in this example represent openings along the bottom surface 110 of the body 102 into which the crossbars 116 can be inserted. The notches 114 in this example also include areas into which the crossbars 116 can be snapped or otherwise coupled, inserted, secured, or attached to the body 102. As a particular example, the notches 114 could represent cavities or grooves that are open along the bottom surface 110 of the body 102, where the cavities or grooves are slightly smaller than the crossbars 116 at or near the bottom surface 110 of the body 102. This may allow, for example, the crossbars 116 to be snapped or otherwise forced through the narrower openings and into the larger portions of the cavities or grooves, thereby retaining the crossbars 116 within the notches 114. The scleral prosthesis 100 could include a single notch 114 for receiving one or more crossbars 114 or multiple notches 114 for receiving multiple crossbars 116.

At least one crossbar 116 inserted into the scleral prosthesis 100 in this example is wider than at least a central portion of the prosthesis 100. For example, a crossbar 116 could be wider than a central portion of the body 102 or wider than the entire body 102. Each crossbar 116 may have any suitable size and shape, such as a straight rod or a bar having wider ends. In this example, each crossbar 116 has a cylindrical barbell-type shape, where a diameter of a central portion of the crossbar 116 is smaller than a diameter of the ends of the crossbar 116. However, the crossbars 116 could have any other suitable size or shape, and different crossbars 116 could have different sizes or shapes. In addition, each crossbar 116 may be inserted into the body 102 of the scleral prosthesis 100 at any suitable location. In this example, the crossbars 116 are inserted into the body 102 near the ends 104-106 of the prosthesis 100. The actual distance of each crossbar 116 to its closest end 104-106 could vary depending on the particular implementation.

Each notch 114 represents any suitable cavity, groove, opening, or other structure in a prosthesis body for receiving and retaining a crossbar 116. Each crossbar 116 includes any suitable bar, rod, or other structure configured to be at least partially inserted into the body 102 of a scleral prosthesis 100.

In this example embodiment, the scleral prosthesis 100 can be implanted within a scleral tunnel in a patient's eye. For example, the body 102 of the scleral prosthesis 100 can be implanted in a scleral tunnel such that the ends 104-106 of the body 102 remain outside of the scleral tunnel. Also, the ends 104-106 of the body 102 could be relatively flat, forming flat bases that lie on the surface of the patient's eye outside of the scleral tunnel. At least one crossbar 116 can be inserted into the body 102 of the scleral prosthesis 100 after the prosthesis 100 has been implanted in the scleral tunnel. In some embodiments, both or all crossbars 116 are inserted into the body 102 of the scleral prosthesis 100 after the body 102 is inserted into the scleral tunnel. In other embodiments, at least one of the crossbars 116 could be inserted into the body 102 of the scleral prosthesis 100 prior to implantation in the scleral tunnel, such as when a crossbar 116 is inserted into an end of the body 102 that will not travel through the scleral tunnel during implantation.

The scleral tunnel in which the body 102 of the scleral prosthesis 100 is implanted can be formed near the ciliary body of a patient's eye. Once implanted in a scleral tunnel, the scleral prosthesis 100 helps to, for example, increase the amplitude of accommodation of the patient's eye. The scleral prosthesis 100 could also help to treat other eye conditions, such as glaucoma, ocular hypertension, elevated intraocular pressure, or other eye disorders. In some embodiments, multiple prostheses (such as four) are implanted in a patient's eye, and the ends of the prostheses are "free" (not attached to the ends of other prostheses).

By making at least one crossbar 116 wider than at least a central portion of the body 102 of the scleral prosthesis 100, various benefits could be obtained, such as stabilization of the prosthesis 100. For example, with at least one wider crossbar 116, it may be less likely that the scleral prosthesis 100 would turn or rotate within a scleral tunnel after implantation. Also, at least one wider crossbar 116 may help to lock the scleral prosthesis 100 into place and impede movement of the scleral prosthesis 100. In addition, at least one wider crossbar 116 may make it less likely that the scleral prosthesis 100 can be inadvertently ejected out of the scleral tunnel after implantation. This may be particularly true when multiple crossbars 116 are wider than the scleral tunnel itself.

Any suitable technique could be used to manufacture or fabricate the body 102 and the crossbars 116, including any of the techniques described in the above-identified patent documents. Similarly, the body 102 and the crossbars 116 could be formed from any suitable material or materials, including any of the materials described in the above-identified patent documents.

In particular embodiments, the body 102 of the scleral prosthesis 100 in FIGS. 1A and 1B may represent a single integrated piece or be formed from multiple pieces. Also, the body 102 could be formed from any suitable material or materials, such as polymethyl methacrylate ("PMMA"), polyether-ether ketone ("PEEK"), or other material(s). Further, each crossbar 116 may represent a single integrated piece or include multiple pieces and can be formed from any suitable material or materials, such as a metal. In addition, the body 102 and the crossbars 116 could have any suitable size, shape, and dimensions, and prostheses 100 of different sizes, shapes, or dimensions could be provided. As a particular example, the crossbars 116 could have an inner edge-to-inner edge distance of 3.95 mm once the crossbars 116 are completely inserted into the body 102.

Although FIGS. 1A and 1B illustrate one example of a scleral prosthesis 100, various changes may be made to FIGS. 1A and 1B. For example, the body 102, notches 114, and/or crossbars 116 could have any other suitable size, shape, or dimensions. Also, the scleral prosthesis 100 could include any suitable number of crossbars 116, including a single crossbar 116 or more than two crossbars 116. In addition, a notch 114 could be replaced with one or more holes that do not open along the bottom of the prosthesis 100 but rather penetrate the sides of the prosthesis 100 in a configuration parallel with the current notches 114. One or more crossbars 116 could then be inserted through the holes and fastened in any suitable fashion.

Figure 2A:
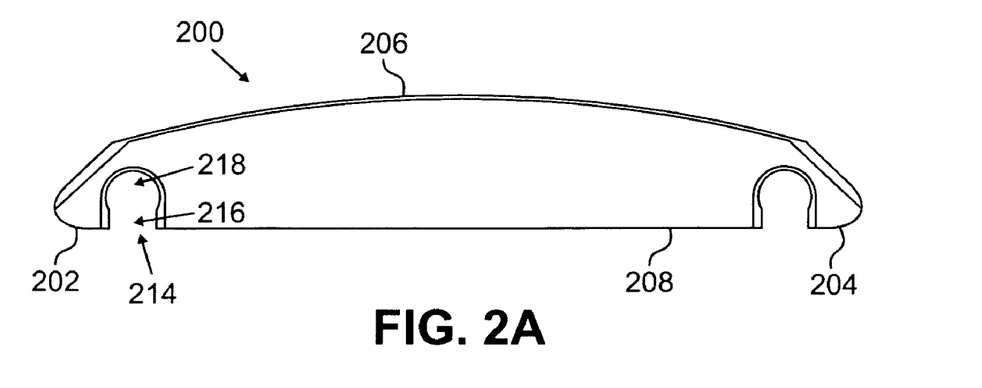
FIGS. 2A through 2C illustrate a first example body of a scleral prosthesis for receiving crossbars in accordance with this disclosure.
Figure 2B:
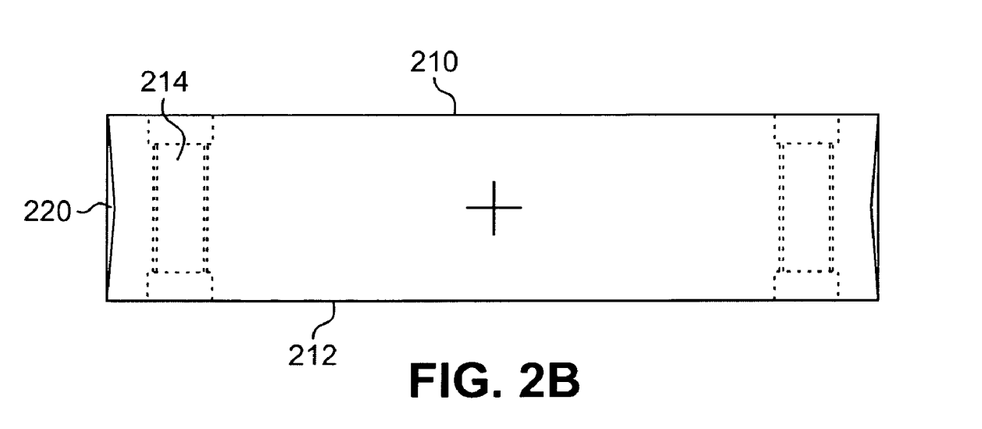
Figure 2C:
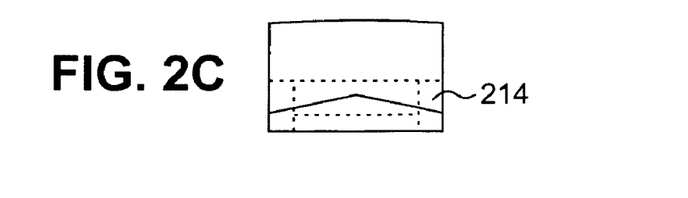

FIGS. 2A through 2C illustrate a first example body 200 of a scleral prosthesis for receiving crossbars in accordance with this disclosure. The embodiment of the scleral prosthesis body 200 shown in FIGS. 2A through 2C is for illustration only. Other embodiments of the scleral prosthesis body 200 could be used without departing from the scope of this disclosure.

In this example, the body 200 includes two free ends 202-204, a top surface 206, a bottom surface 208, and sides 210-212. As shown here, the top surface 206 is generally convex with smaller concave portions near the ends 202-204. Also, the bottom surface 208 and the sides 210-212 are generally flat. In this example embodiment, each of the ends 202-204 generally includes a rounded tip, which represents the transition from the flatter bottom surface 208 and the concave portion of the top surface 206. However, each of these surfaces could have any other suitable size, shape, or dimensions, such as when the bottom surface 208 is at least partially curved.

As shown here, the body 200 includes two notches 214, which form grooves, indentations, or other cavities within the scleral prosthesis body 200. Each of the notches 214 in this example includes a relatively narrower opening portion 216 and a relatively wider retaining portion 218. In this example, the opening portion 216 represents the part of the notch 214 that is open along the bottom surface 208 of the body 200. The retaining portion 218 represents the part of the notch 214 that is accessible through the opening portion 216. The opening portion 216 may be somewhat smaller than the crossbar that is inserted into the notch 214, while the retaining portion 218 may approximately match or be somewhat larger than the crossbar that is inserted into the notch 214. This allows the crossbar to be snapped into or otherwise placed within the notch 214, while reducing the chances that the crossbar could inadvertently leave or be ejected from the notch 214.

This represents only one example mechanism by which the crossbars 116 could be inserted into and retained in the notches 214. Any other suitable technique could be used to secure or retain a crossbar within a notch 214. Other techniques could include using an adhesive, a suture, male and female or other interlocking parts, or any other suitable mechanical or other attachment or coupling mechanism. As another example, the notches 214 could be sized to receive the crossbars, and pressure from a patient's eye on the crossbars could maintain the crossbars within the notches 214. In addition, the crossbars 116 could be inserted into holes on the sides of the prosthesis approximately in the same location as the notches 214.

In this example, the opening portion 216 and the retaining portion 218 of each notch 214 are generally arranged perpendicular to the bottom surface 208 of the body 200. However, the notches 214 could have any other suitable arrangement. For example, as shown in FIGS. 1A and 1B, the opening portion 216 of each notch 214 could be located closer to a central portion of the body 200 than its associated retaining portion 218.

In this particular embodiment, each notch 214 is generally configured to receive a barbell-type crossbar, where ends of each notch 214 (located along the sides 210-212) are wider than a middle portion of the each 214. This is for illustration only. Notches 214 having other or additional shapes could also be used in the body 200.

As shown in FIG. 2B, each end 202-204 of the body 200 could be angled or include a small groove 220 in its top surface 206. The groove 220 represents a portion of the top surface 206 that is generally angled inward and downward. Among other things, the groove 220 could be used to facilitate pushing or pulling the body 200 into a scleral tunnel during implantation.

The body 200 could have any suitable dimensions. For example, the body 200 could be 5.4 mm long (measured end 202 to end 204), 1.38 mm wide (measured side 210 to side 212), and 0.93 mm tall at its peak (measured top 206 to bottom 208). The top surface 206 could have a radius of curvature of 9.0 mm. The notches 214 could have a center-to-center distance of 4.4 mm, and the distance from each notch's center to the nearest end 202 or 204 could equal 0.5 mm. Each of the notches 214 could have a width (measured side 210 to side 212) of 1.38 mm. The central portion of each notch 214 could have a diameter of 0.4 mm, and the ends of each notch 214 could have a diameter of 0.45 mm. The ends of each notch 214 may be 0.2 mm in width (measured side 210 to side 212). These dimensions are for illustration only.

Although FIGS. 2A through 2C illustrate one example of a body 200 of a scleral prosthesis for receiving crossbars, various changes may be made to FIGS. 2A through 2C. For example, the body 200 and notches 214 could each have any other suitable size, shape, or dimensions. Also, the body 200 could include any suitable number of notches 214, including a single notch 214 or more than two notches 214. In addition, the body 200 could have one or more holes into which the crossbars could be placed, such as holes approximately in the same locations as the notches 214.

Figure 3A:
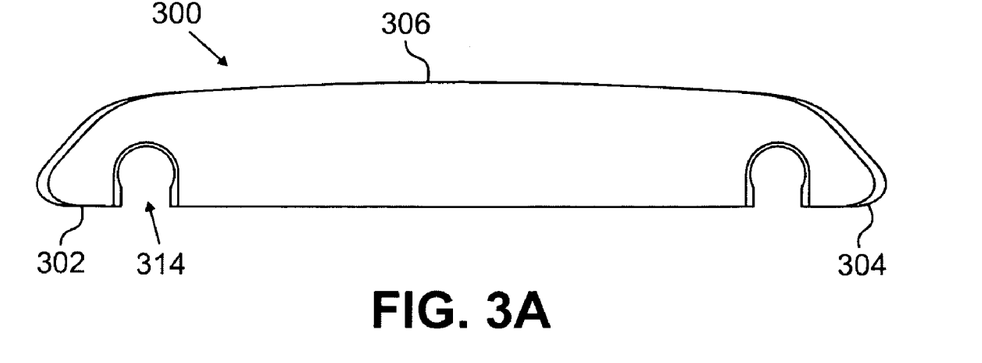
FIGS. 3A through 3C illustrate a second example body of a scleral prosthesis for receiving crossbars in accordance with this disclosure.
Figure 3B:
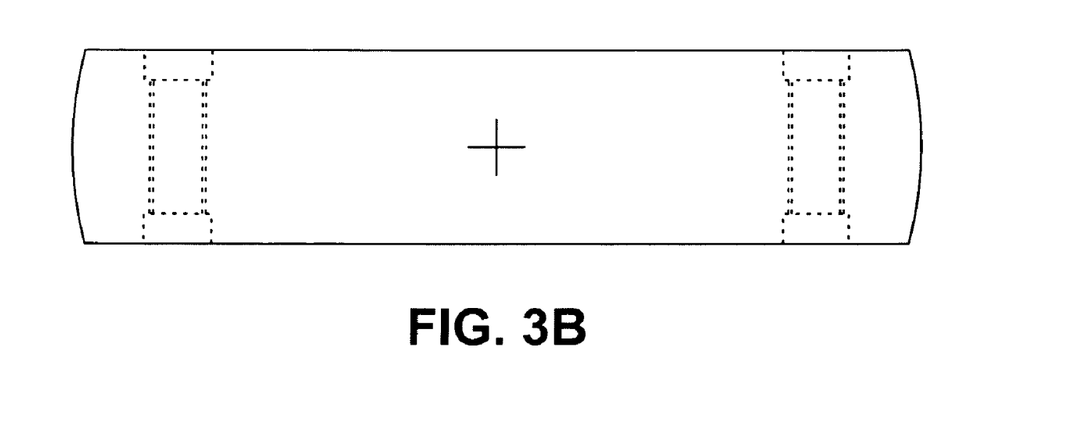
Figure 3C:
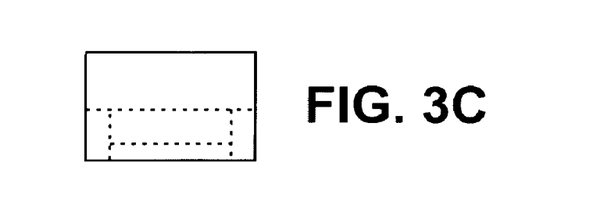

FIGS. 3A through 3C illustrate a second example body 300 of a scleral prosthesis for receiving crossbars in accordance with this disclosure. The embodiment of the scleral prosthesis body 300 shown in FIGS. 3A through 3C is for illustration only. Other embodiments of the scleral prosthesis body 300 could be used without departing from the scope of this disclosure.

In this example, the scleral prosthesis body 300 is similar in size and shape to the scleral prosthesis body 200 of FIGS. 2A through 2C. In this example embodiment, however, ends 302-304 of the body 300 are generally more rounded than the ends 202-204 of the body 200. The ends 302-304 of the body 300 also lack notches 220 or similar inward surface structures. In addition, a top surface 306 of the body 300 has a larger radius of curvature than the top surface 206, and the top surface 306 is generally steeper at the ends 302-304 when compared to the top surface 206. The body 300 is otherwise the same as or similar to the body 200.

As shown here, the body 300 includes two notches 314, which form grooves, indentations, or other cavities within the body 300. Each of the notches 314 can receive and retain a crossbar associated with a scleral prosthesis. Each notch 314 in this example, by its shape, can retain a crossbar within the body 300. However, any other suitable technique could be used to secure or retain a crossbar, such as holes extending through the sides of the prosthesis. Also, the notches 314 could have the same or similar shape or arrangement as shown in FIGS. 1A and 1B. In addition, while each notch 314 in this example is generally configured to receive a barbell-type crossbar, notches 314 having other or additional shapes could also be used in the body 300.

The body 300 could have any suitable dimensions. For example, the body 300 could be 5.9 mm long, 1.38 mm wide, and 0.93 mm tall at its peak. The top surface 306 could have a radius of curvature of 20.0 mm. The notches 314 could have a center-to-center distance of 4.4 mm, and the distance from each notch's center to the nearest end 302 or 304 could equal 0.75 mm. A distance between (i) a line tangent to the top of a notch 314 and (ii) the top surface 306 could equal 0.37 mm. Also, a distance between (i) the slanted surface at an end of the body 300 and (ii) a line parallel to the slanted surface and tangent to the notch 314 could also equal 0.37 mm. Each of the notches 314 could have a width of 1.38 mm. The central portion of each notch 314 could have a diameter of 0.4 mm, and the ends of each notch 314 could have a diameter of 0.45 mm. The ends of each notch 314 may each be 0.2 mm in width. These dimensions are for illustration only.

Although FIGS. 3A through 3C illustrate another example of a body 300 of a scleral prosthesis for receiving crossbars, various changes may be made to FIGS. 3A through 3C. For example, the body 300 and notches 314 could each have any other suitable size, shape, or dimensions. Also, the body 300 could include any suitable number of notches 314, including a single notch 314, more than two notches 314, or one or more holes.

Figure 4A:
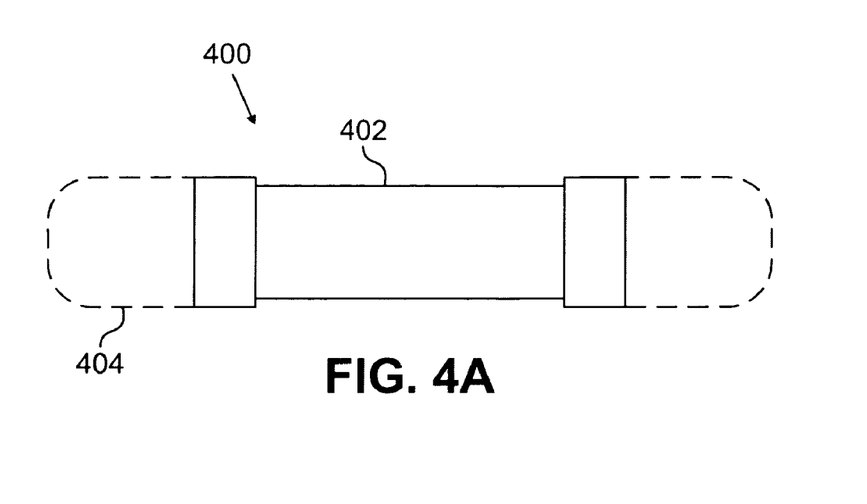
FIGS. 4A and 4B illustrate an example crossbar for use with a scleral prosthesis in accordance with this disclosure.
Figure 4B:
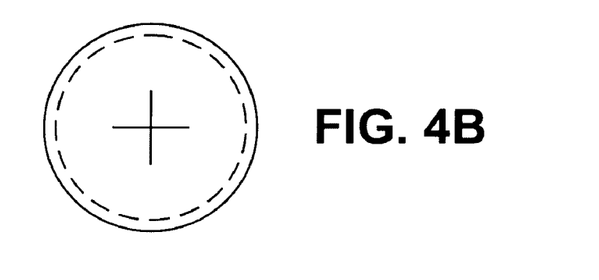
Figure 5A:
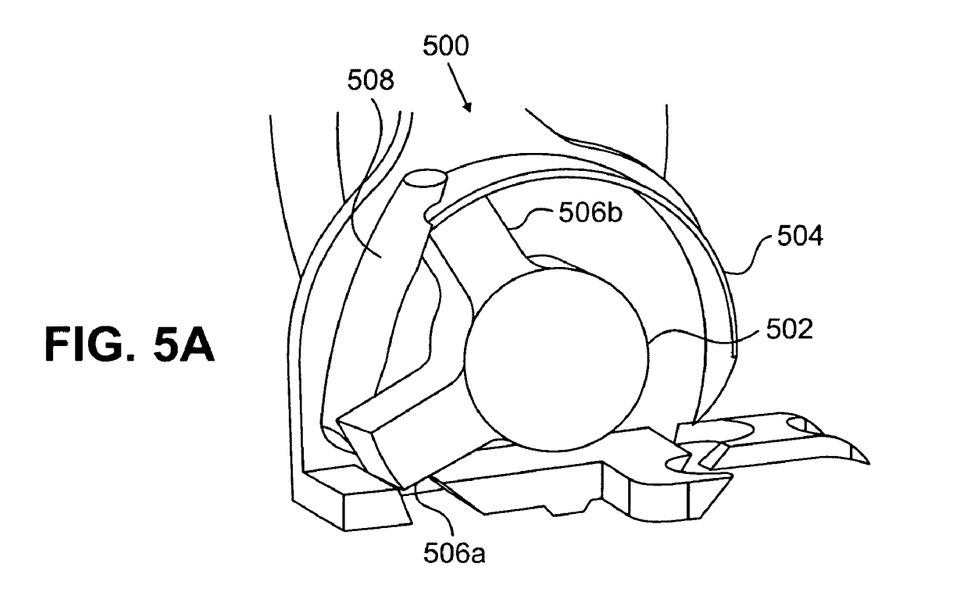
FIGS. 5A through 5D illustrate an example surgical tool for depositing a scleral prosthesis into a scleral tunnel in accordance with this disclosure.
Figure 5B:
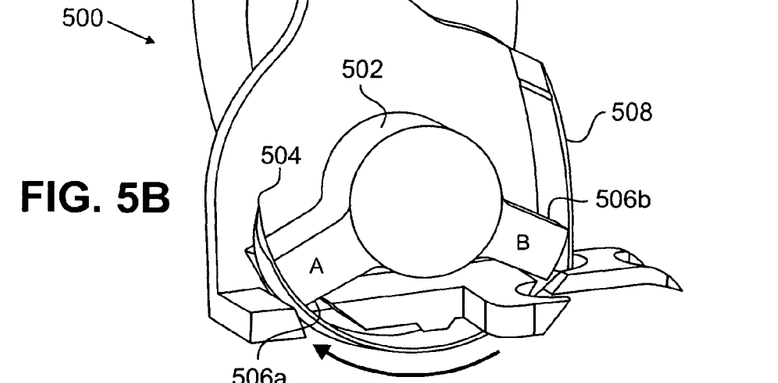
Figures 5C, 5D:
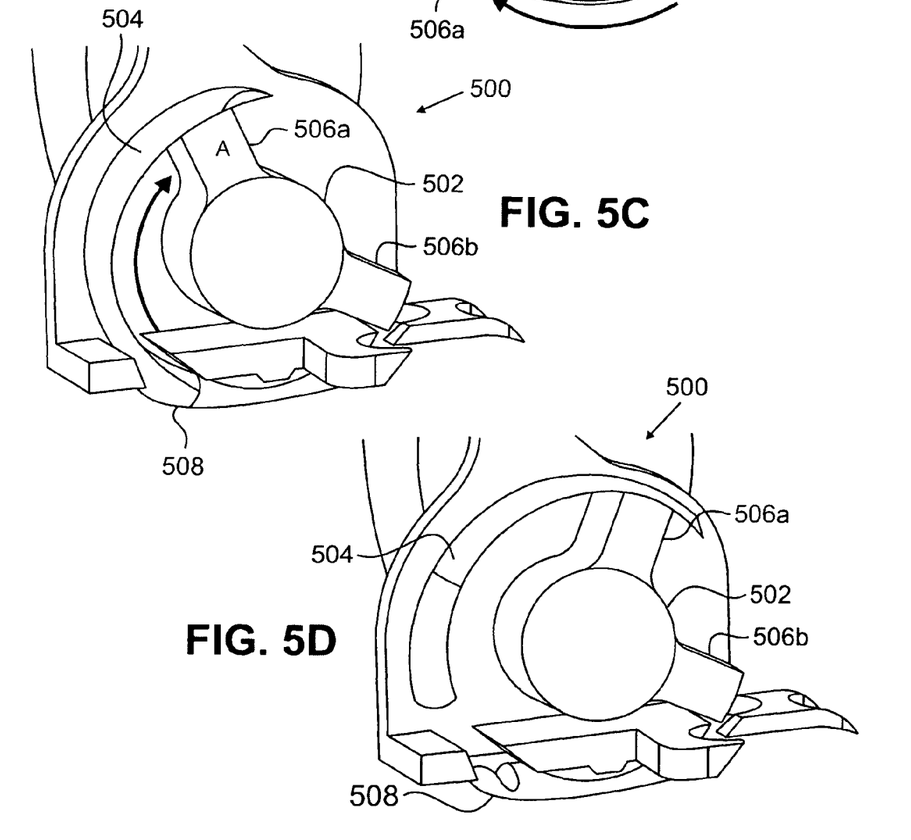

FIGS. 4A and 4B illustrate an example crossbar 400 for use with a scleral prosthesis in accordance with this disclosure. The embodiment of the crossbar 400 shown in FIGS. 4A and 4B is for illustration only. Other embodiments of the crossbar 400 could be used without departing from the scope of this disclosure.

In this example, the crossbar 400 includes a central portion 402 and end portions 404. As shown here, the central portion 402 has a cylindrical shape with a circular or substantially circular cross section. The end portions 404 also have cylindrical shapes with circular or substantially circular cross sections. In this particular embodiment, the central portion 402 has a smaller diameter or cross sectional area than each of the end portions 404.

In this example, the central portion 402 could have a diameter of 0.4 mm, and the end portions 404 could each have a diameter of 0.45 mm. The central portion 402 could be 1.05 mm in length (measured end-to-end), and each end portion 404 could be at least 0.2 mm in length. As shown in FIGS. 2C and 3C, this completely fills a notch in a prosthesis body. One end portion 404 can have an additional length (denoted X1), and the other end portion 404 can have an additional length (denoted X2). In particular embodiments, X1 and X2 both equal 0.5 mm, giving each end portion 404 a total length of 0.7 mm. In other particular embodiments, X1 equals 0.0 mm and X2 equals 11.0 mm, giving the end portions 404 a total length of 0.2 mm and 1.2 mm, respectively.

Although FIGS. 4A and 4B illustrate an example crossbar 400 for use with a scleral prosthesis, various changes may be made to FIGS. 4A and 4B. For example, the crossbar 400 could have any other suitable size, shape, or dimensions. Also, the crossbar 400 could include any number of sections or portions having a different diameter or cross sectional area, including none or more than two.

FIGS. 5A through 5D illustrate an example surgical tool 500 for depositing a scleral prosthesis into a scleral tunnel in accordance with this disclosure. The embodiment of the surgical tool 500 shown in FIGS. 5A through 5D is for illustration only. Other embodiments of the surgical tool 500 could be used without departing from the scope of this disclosure.

In this example, the surgical tool 500 includes a central portion 502, a cutting blade 504, and hub arms 506a-506b. The central portion 502 can be rotated in multiple directions to move the cutting blade 504 into and out of the scleral tissue of a patient's eye. The hub arms 506a-506b couple the central portion 502 to the cutting blade 504, helping to translate rotation of the central portion 502 into movement of the cutting blade 504.

A body 508 of a scleral prosthesis is engaged with the tail end of the cutting blade 504. The body 508 could represent any suitable prosthesis body, such as any of the prosthesis bodies described above. As shown here, the cutting blade 504 is initially rotated through the scleral tissue of a patient's eye using the hub arm 506b. Eventually, the hub arm 506a engages with the tip of the cutting blade 504, and the hub arm 506b disengages from the cutting blade 504. The hub arm 506a then continues to rotate the cutting blade 504 through the scleral tissue and out of the newly formed scleral tunnel. In this example, the scleral prosthesis body 508 is pulled into the scleral tunnel upside-down by the cutting blade 504 and then disengages from the cutting blade 504. The prosthesis body 508 can then be rotated to properly position the prosthesis body 508 in the newly-formed scleral tunnel. At this point, one or more crossbars can be inserted into or coupled or attached to the body 508, forming a completed scleral prosthesis.

The technique shown in FIGS. 5A through 5D is for illustration only. Any other suitable technique could be used to implant a scleral prosthesis into a scleral tunnel. For example, the surgical tool 500 could include a single hub arm, and the surgical tool 500 could rotate the cutting blade 504 into scleral tissue and then out of the scleral tissue to form a scleral tunnel. The prosthesis body 508 could then be inserted into the scleral tunnel using any other suitable tool or technique.

Although FIGS. 5A through 5D illustrate an example surgical tool 500 for depositing a scleral prosthesis into a scleral tunnel, various changes may be made to FIGS. 5A through 5D. For example, any other suitable technique could be used to form a scleral tunnel in a patient's eye. The formation of the scleral tunnel may or may not include the simultaneous or near-simultaneous implantation of a scleral prosthesis body into the scleral tunnel.

Figure 6:
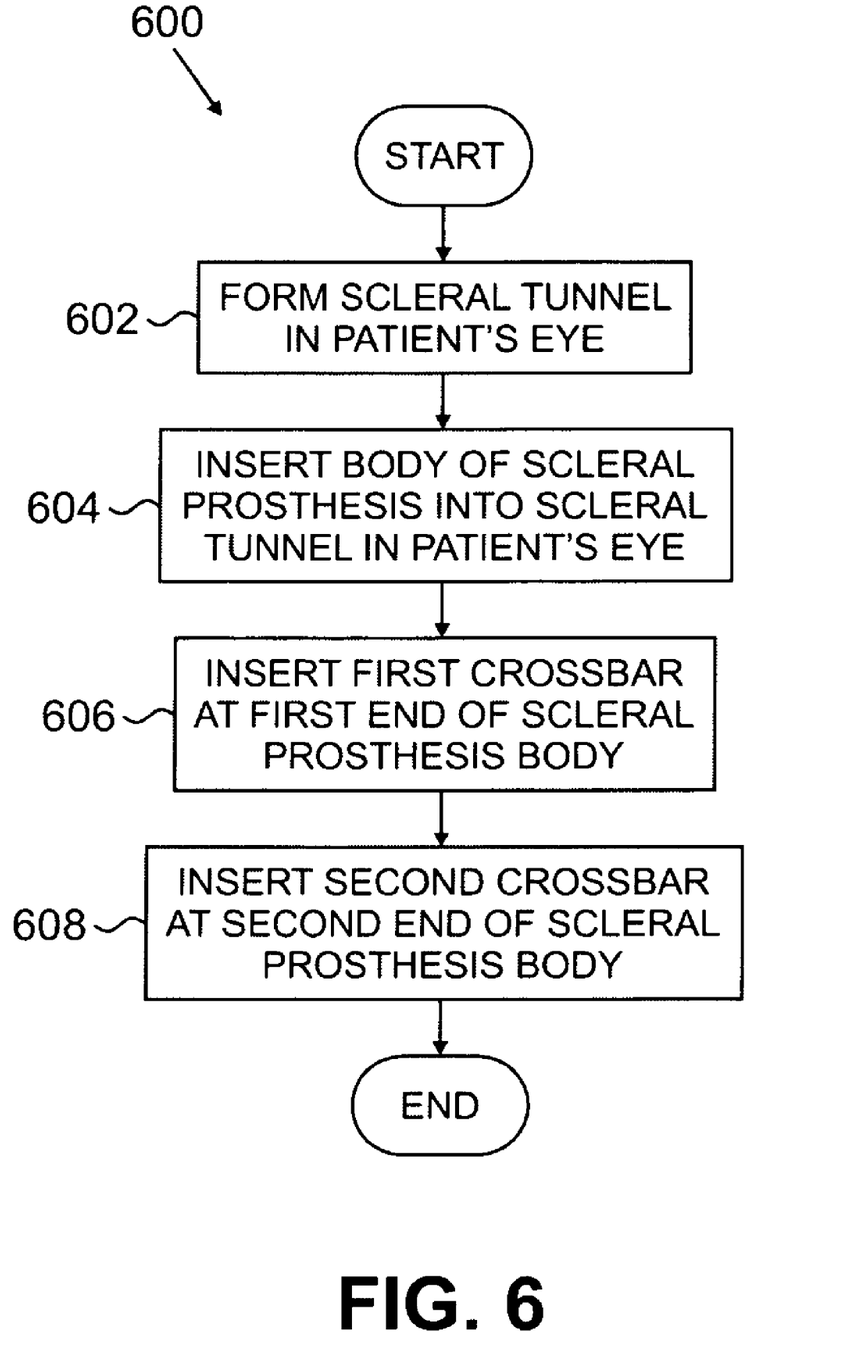
FIG. 6 illustrates an example method for inserting a scleral prosthesis into a patient's eye in accordance with this disclosure.

FIG. 6 illustrates an example method 600 for inserting a scleral prosthesis into a patient's eye in accordance with this disclosure. The embodiment of the method 600 shown in FIG. 6 is for illustration only. Other embodiments of the method 600 could be used without departing from the scope of this disclosure.

A scleral tunnel is formed in the scleral tissue of a patient's eye at step 602. This could include, for example, using a curved cutting blade to form the scleral tunnel. Examples of surgical tools for forming scleral tunnels are described above and in the above-incorporated patent documents. Any other suitable tool or technique could be used to form any suitable scleral tunnel in scleral tissue.

A body of the scleral prosthesis is inserted into the scleral tunnel at step 604. This could include, for example, inserting the prosthesis body into the scleral tunnel while the scleral tunnel is being formed. This could also include inserting the prosthesis body into the scleral tunnel after formation of the scleral tunnel.

A first crossbar is inserted into a first end of the scleral prosthesis body at step 606. This could include, for example, inserting a crossbar 116 into one notch 114 of the scleral prosthesis body. The crossbar 116 could be snapped into the notch 114 or otherwise secured or attached to the scleral prosthesis body. The crossbar 116 could also be forced into the notch 114 without actually being secured in the notch 114, such as when pressure from the patient's eye holds the crossbar 116 in the notch 114. Depending on the implementation, the central portion of the crossbar 116 may or may not be completely within the body of the scleral prosthesis. For instance, a portion of the crossbar 116 could partially reside outside of the body 102 or extend out of the bottom surface 108 of the body 102.

A second crossbar is inserted into a second end of the scleral prosthesis body at step 608. This could include, for example, inserting another crossbar 116 into another notch 114 in the scleral prosthesis body 102. Depending on the implementation, the second crossbar 116 may or may not be inserted into the body 102 of the prosthesis in the same way as the first crossbar 116. Also, the first and second crossbars 116 could be identical, or they could differ in size, shape, or dimensions.

Although FIG. 6 illustrates one example of a method 600 for inserting a scleral prosthesis into a patient's eye, various changes may be made to FIG. 6. For example, while shown as a series of steps, various steps in FIG. 6 could overlap or occur in parallel. As a particular example, steps 602-604 could overlap when a surgical tool is used to form a scleral tunnel and insert a scleral prosthesis body. Also, while shown as including two crossbars, the scleral prosthesis could include one or more than two crossbars. In addition, as noted above, one of the crossbars could be inserted into the scleral prosthesis body before the prosthesis body is inserted into a patient's eye.

It may be advantageous to set forth definitions of certain words and phrases used throughout this patent document. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A scleral prosthesis comprising:
a prosthesis body comprising:
first and second side surfaces extending along a longer dimension of the prosthesis body; and
a cavity extending through the prosthesis body from the first side surface to the second side surface across a shorter dimension of the prosthesis body; and
a crossbar configured to be inserted into the cavity, the crossbar wider than the prosthesis body;
wherein the cavity comprises an opening portion along a bottom surface of the prosthesis body and a retaining portion within the prosthesis body;
wherein the retaining portion is configured to receive the crossbar when the crossbar is inserted through the opening portion;
wherein the opening portion is narrower than the retaining portion and is configured to retain the crossbar in the retaining portion;
wherein the opening and retaining portions are wider at their ends; and
wherein the crossbar has wider ends.

2. A scleral prosthesis comprising:
a prosthesis body configured to be inserted into a scleral tunnel within scleral tissue of an eye, the prosthesis body comprising:
first and second side surfaces; and
a cavity extending through the prosthesis body from the first side surface to the second side surface; and
a crossbar configured to be inserted into the cavity, the crossbar wider than the prosthesis body;
wherein the cavity comprises:
an opening portion along a bottom surface of the prosthesis body; and
a retaining portion within the prosthesis body;
wherein the retaining portion is configured to receive the crossbar when the crossbar is inserted through the opening portion; and
wherein the opening portion is narrower than the retaining portion and is configured to retain the crossbar in the retaining portion.

3. The scleral prosthesis of claim 2, wherein the opening portion and the retaining portion are aligned along a line perpendicular to the bottom surface of the prosthesis body.

4. A scleral prosthesis comprising:
a prosthesis body configured to be inserted into a scleral tunnel within scleral tissue of an eye, the prosthesis body comprising:
first and second side surfaces; and
a cavity extending through the prosthesis body from the first side surface to the second side surface; and
a crossbar configured to be inserted into the cavity, the crossbar wider than the prosthesis body;
wherein:
the cavity defines a narrower central opening and wider end openings; and the crossbar has a narrower central portion and wider end portions.

5. The scleral prosthesis of claim 4, wherein the wider end portions of the crossbar are unequal in length.

6. The scleral prosthesis of claim 1, wherein:
the prosthesis body comprises multiple cavities; and
the scleral prosthesis comprises multiple crossbars configured to be inserted into the multiple cavities.

7. The scleral prosthesis of claim 6, wherein each of the cavities is located proximate to an end of the prosthesis body.

8. The scleral prosthesis of claim 1, wherein:
a bottom surface of the prosthesis body is flat; and
a top surface of the prosthesis body is curved.

9. The scleral prosthesis of claim 1, wherein at least one end of the prosthesis body comprises a groove angled inward and downward towards a bottom surface of the prosthesis body.

10. The scleral prosthesis of claim 1, wherein the crossbar is substantially straight and cylindrical.

11. A scleral prosthesis body comprising:
first and second free ends;
first and second side surfaces extending along a longer dimension of the prosthesis body; and
a cavity extending through the scleral prosthesis body from the first side surface to the second side surface across a shorter dimension of the prosthesis body, the cavity configured to receive and retain a crossbar inserted into the cavity;
wherein the cavity comprises an opening portion along a bottom surface of the prosthesis body and a retaining portion within the prosthesis body;
wherein the retaining portion is configured to receive the crossbar when the crossbar is inserted through the opening portion;
wherein the opening portion is narrower than the retaining portion and is configured to retain the crossbar in the retaining portion; and
wherein the opening and retaining portions are wider at their ends.

12. A scleral prosthesis body comprising:
first and second free ends;
first and second side surfaces; and
a cavity extending through the scleral prosthesis body from the first side surface to the second side surface, the cavity configured to receive a crossbar inserted into the cavity;
wherein the cavity comprises:
an opening portion along a bottom surface of the prosthesis body; and
a retaining portion within the prosthesis body;
wherein the retaining portion is configured to receive the crossbar when the crossbar is inserted through the opening portion;
wherein the opening portion is narrower than the retaining portion and is configured to retain the crossbar in the retaining portion; and
wherein the prosthesis body is configured to be inserted into a scleral tunnel within scleral tissue of an eye.

13. The scleral prosthesis body of claim 12, wherein the opening portion and the retaining portion are aligned along a line perpendicular to the bottom surface of the prosthesis body.

14. A scleral prosthesis body comprising:
first and second free ends;
first and second side surfaces; and
a cavity extending through the scleral prosthesis body from the first side surface to the second side surface, the cavity configured to receive a crossbar inserted into the cavity, wherein the cavity defines a narrower central opening and wider end openings; and
wherein the prosthesis body is configured to be inserted into a scleral tunnel within scleral tissue of an eye.

15. The scleral prosthesis body of claim 14, wherein the wider end openings of the cavity are unequal in length.

16. The scleral prosthesis body of claim 11, wherein the prosthesis body comprises multiple cavities configured to receive multiple crossbars.

17. The scleral prosthesis body of claim 16, wherein each of the cavities is located proximate to one of the ends of the scleral prosthesis body.

18. The scleral prosthesis body of claim 11, wherein at least one of the ends of the scleral prosthesis body comprises a groove angled inward and downward towards a bottom surface of the scleral prosthesis body.

19. A method comprising:
inserting a scleral prosthesis body into ocular tissue of a patient's eye; and
inserting a crossbar into a cavity of the scleral prosthesis body after insertion of the scleral prosthesis body into the ocular tissue, the crossbar wider than the scleral prosthesis body, the cavity extending through the scleral prosthesis body from a first side surface to a second side surface of the scleral prosthesis body, the first and second side surfaces extending along a longer dimension of the prosthesis body, the cavity extending across a shorter dimension of the prosthesis body;
wherein the cavity comprises:
an opening portion along a bottom surface of the prosthesis body; and
a retaining portion within the prosthesis body;
wherein the retaining portion receives the crossbar when the crossbar is inserted through the opening portion; and
wherein the opening portion is narrower than the retaining portion and retains the crossbar in the retaining portion.

20. The method of claim 19, wherein:
inserting the scleral prosthesis body into ocular tissue comprises inserting the scleral prosthesis body into a scleral tunnel; and
inserting the crossbar into the cavity of the scleral prosthesis body comprises inserting multiple crossbars into multiple cavities of the scleral prosthesis body, at least one crossbar located outside of the scleral tunnel at each end of the scleral prosthesis body.

21. The scleral prosthesis body of claim 12, wherein the scleral prosthesis body is configured to expand a portion of a sclera of the eye when implanted in the scleral tunnel in order to increase an effective working distance of a ciliary muscle of the eye.

* * * * *